(12) United States Patent
Pepe et al.

(10) Patent No.: US 8,349,570 B2
(45) Date of Patent: Jan. 8, 2013

(54) ENHANCING ENDOTOXIN DETECTION

(75) Inventors: Michael G. Pepe, Birmingham, AL (US); Milton Keith Champion, Hoover, AL (US)

(73) Assignee: BioDtech, Inc., Birmingham, AL (US)

( * ) Notice: Subject to any disclaimer, the term of this patent is extended or adjusted under 35 U.S.C. 154(b) by 0 days.

(21) Appl. No.: 12/880,993

(22) Filed: Sep. 13, 2010

(65) Prior Publication Data
US 2011/0020854 A1 Jan. 27, 2011

Related U.S. Application Data

(62) Division of application No. 12/193,169, filed on Aug. 18, 2008, now Pat. No. 7,846,678.

(51) Int. Cl.
G01N 33/53 (2006.01)
G01N 33/554 (2006.01)
G01N 33/567 (2006.01)

(52) U.S. Cl. .......................... 435/7.1; 435/7.2; 435/7.32

(58) Field of Classification Search ........................ None
See application file for complete search history.

(56) References Cited

U.S. PATENT DOCUMENTS

| | | | |
|---|---|---|---|
| 3,962,039 A | 6/1976 | Bates | |
| 4,695,392 A | 9/1987 | Whitehead et al. | |
| 5,308,834 A | 5/1994 | Scott et al. | |
| 6,719,973 B1 | 4/2004 | Ding et al. | |
| 6,849,426 B2 | 2/2005 | Chen et al. | |
| 7,297,551 B2 | 11/2007 | Ding et al. | |
| 2007/0123466 A1* | 5/2007 | Salmon et al. | 514/14 |
| 2007/0160984 A1 | 7/2007 | Huang et al. | |
| 2008/0085865 A1 | 4/2008 | Ding et al. | |

OTHER PUBLICATIONS

Ghetie et al (Journal of Immunological Methods vol. 112, pp. 267-277, 1988).*
Asakawa et al., Application of the Limulus test for practical quality control on endotoxin content in commercial human serum albumin (HSA) products. In comparison with the rabbit pyrogen test, Yakugaku. Zasshi, 114(11):888-893 (1994.
Creput et al., New therapeutic targets for antibodies and recombinant proteins in organ transplantation, Curr. Opin. Mol. Ther., 9(2)153-159 (2007).
David, The Interaction of Lipid A and Lipopolysaccharide with Human Serum Albumin. In: Brade, H., ed. Endotoxin in Health and Disease. New York: Marcel-Dekker, Inc., pp. 413-422 (1999).
Ding et al., High-performance affinity capture-removal of bacteial pyrogen from solutions, J. Chromatogr. B Biomed. Sci. Appl., 759(2):237-246 (2001).
Ding et al, The Sushi peptides: structural characterization and mode of action against gram-negative bacteria, Cell. Mol. Life Sci., 65:1202-1219 (2008).
Dubel, Recombinant therapeutic antibodies, Appl. Microbiol. Biotechnol., 74(4):723-729 (2007).

Dubose et al., Comparison of Plasma Extraction Techniques in Preparation of Samples for Endotoxin Testing by the Limulus Amoebocyte Lysate Test, J. Clinical Microbiology, 11(1):68-72 (1980).
Hulko et al., Inherent chaperone-like activity of aspartic proteases reveals a distant evolutionary relation to double-ψbarrel domains of AAA-ATPases, Protein Science, 16:644-653 (2007).
Jurgens et al., Investigation into the interaction of recombinant human serum albumin with Re-lipopolysaccharide and lipid A, J. Endotoxin. Res., 8:115-126 (2002).
Kaca et al., Hemoglobin, a newly recognized lipopolysaccharide (LPS)-binding protein that enhances LPS biological activity, J. Biol. Chem., 269(4):25078-25084 (1994).
Li et al., Molecular mechanisms that govern the specificity of sushi peptides for gram-negative bacterial membrane lipids, Biochemistry. 45(35):10554-10562 (2006).
Li et al., The specificity of sushi peptides for endotoxin and anionic phospholipids: potential application of POPG as an adjuvant for anti-LPS strategies, Biochem. Soc. Trans., 34(2):270-272 (2006).
Nayeem et al., Recombinant antibodies in cancer therapy, Curr. Protein Pept. Sci., 7(2):165-170 (2006).
Obayashi, Addition of perchloric acid to blood samples for colorimetric limulus test using chromogenic substrate: comparison with conventional procedures and clinical applications, J. Lab. Clin. Med., 104(3):321-330 (1984).
Petsch et al., Proteinase K digestion of proteins improves detection of bacterial endotoxins by the Limulus amoebocyte lysate assay: application for endotoxin removal from cationic proteins, Anal. Biochem., 259(1):42-47 (1998).
Rao et al., Molecular and biotechnological aspects of microbial proteases, Microbiology & Mol. Biol. Rev., 62(3):597-635 (1998).
Rasmussen et al., Manufacture of recombinant polyclonal antibodies, Biotechnol. Lett., 29(6):845-852 (2007).
Richter et al., Mechanism of activation of the gastric aspartic proteinases: pepsinogen, progastricsin and prochymosin, Biochem. J., 335:481-490 (1998).
Rietschel et al., Pyrogenicity and immunogenicity of lipid A complexed with bovine serum albumin or human serum albumin, Infect. Immun., 8(2):173-177 (1973).
Roth et al., Optimization of detection of bacterial endotoxin in plasma with the Limulus test, J. Lab. Clin. Med., 116(2):153-161 (1990).
Roth et al., Production of modified crosslinked cell-free hemoglobin for human use: the role of quantitative determination of endotoxin contamination, Transfusion, 33(11):919-924 (1993).
Roth, Hemoglobin enhances the production of tissue factor by endothelial cells in response to bacterial endotoxin, Blood, 83(10):2860-2865 (1994).
Roth et al., Toxicity of hemoglobin solutions: hemoglobin is a lipopolysaccharide (LPS) binding protein which enhances LPS biological activity, Artif. Cells Blood Substit. Immobil. Biotechnol., 22(3)387-398 (1994).

(Continued)

*Primary Examiner* — Albert Navarro
(74) *Attorney, Agent, or Firm* — Meunier Carlin & Curfman, LLC

(57) ABSTRACT

Provided herein are methods for detecting gram negative bacteria or lipopolysaccharide in a sample. Kits for detecting gram negative bacteria or lipopolysaccharide in a sample are provided.

6 Claims, 2 Drawing Sheets

OTHER PUBLICATIONS

Rudbach et al., Restoration of endotoxin activity following alteration by plasma, Nature, 202:811-812 (1964).

Tan et al., Definition of endotoxin binding sites in horseshoe crab factor C recombinant sushi proteins and neutralization of endotoxin by sushi peptides, FASEB J., 14(12):1801-1813 (2000).

Tsuji et al., Use of Magnesium to Increase Sensitivity of Limulus Amoebocyte Lysate for Detection of Endotoxin, Applied Environ. Microbiology, 45(4):1342-1350 (1983).

Westphal et al., Extraction of bacteria with phenol/water, Naturforsch. B: Anorg. Chem. Org. Chem. Biochem. Biophys. Biol., 7B:148-155 (1952).

Xuan et al., In vitro reduction of endotoxin concentrations with the 5S fragment of immunoglobulin G, Antimicrob. Agents Chemother., 41(7):1512-1516 (1997).

Xuan et al., Circulating tumor necrosis factor-alpha production during the progression of rat endotoxic sepsis, Chemotherapy, 47(3):194-202 (2001).

Yentis et al., The effects of IgG and immune complexes on the endotoxin-induced cytokine response, Cytokine, 6 (3):247-254 (1994).

Zhang et al., Differential Blocking of Coagulation-Activating Pathways of Limulus Amebocyte Lysate, J. Clin. Microbiology, 32(6):1537-1541 (1994).

Office Action for EP Application No. 09808609.3 dated Jun. 27, 2012.

Endoprep (TM), BioDtech Inc. Application notes, Sep. 28, 2008, pp. 1-10, XP55030412, Birmingham, AL 35209 USA retrieved from the internet: URL:http://www.biodtechinc.com/doc/prod_endoprep.pdf [retrieved on Jun. 19, 2012].

* cited by examiner

LPS Recovery in BSA Samples

Effect of Pepsin on rFC Activity ly, proteins binding to endotoxin can cause either inhibition or enhancement in the standard assays resulting in false positives and negatives, as well as affecting accuracy. For example, serine protease inhibitors, such as, soybean trypsin inhibitor, alpha2 macroglobulin, aprotinin, anti-plasmin, anti-thrombin III, anti-trypsin and hirudin, inhibit methods of detecting endotoxin. As described in the examples below, treatment of such samples, including serum and blood samples, with an acidic protease degrades the proteins in the sample without affecting endotoxin, thus, increasing the accuracy of endotoxin detection assays. The acidic proteases can be used in, for example, LAL, Factor C and cytokine ELISA assays. There are a variety of assays for the diagnosis of gram negative bacterial infections. The current assay used by pharmaceutical and medical industries is based on a substance called *Limulus Amebocyte* Lysate (LAL). The lysate contains proteins that react in the presence of endotoxins.

SEQUENCE LISTING

```
<160> NUMBER OF SEQ ID NOS: 8

<210> SEQ ID NO 1
<211> LENGTH: 34
<212> TYPE: PRT
<213> ORGANISM: Artificial Sequence
<220> FEATURE:
<223> OTHER INFORMATION: Sushi 1 Peptide

<400> SEQUENCE: 1

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
```

```
                       20                  25                  30

Ser Ser

<210> SEQ ID NO 2
<211> LENGTH: 59
<212> TYPE: PRT
<213> ORGANISM: Artificial Sequence
<220> FEATURE:
<223> OTHER INFORMATION: Sushi 2 Peptide

<400> SEQUENCE: 2

Glu Cys Ala Met Val Ser Ser Pro Glu His Gly Lys Val Asn Ala Leu
1               5                   10                  15

Ser Gly Asp Met Ile Glu Gly Ala Thr Leu Arg Phe Ser Cys Asp Ser
            20                  25                  30

Pro Tyr Tyr Leu Ile Gly Gln Glu Thr Leu Thr Cys Gln Gly Asn Gly
        35                  40                  45

Gln Trp Asn Gly Gln Ile Pro Gln Cys Lys Asn
    50                  55

<210> SEQ ID NO 3
<211> LENGTH: 34
<212> TYPE: PRT
<213> ORGANISM: Artificial Sequence
<220> FEATURE:
<223> OTHER INFORMATION: Sushi 3 Peptide

<400> SEQUENCE: 3

His Ala Glu His Lys Val Lys Ile Gly Val Gln Lys Tyr Gly Gln
1               5                   10                  15

Phe Pro Gln Gly Thr Glu Val Thr Tyr Thr Cys Ser Gly Asn Tyr Phe
            20                  25                  30

Leu Met

<210> SEQ ID NO 4
<211> LENGTH: 34
<212> TYPE: PRT
<213> ORGANISM: Artificial Sequence
<220> FEATURE:
<223> OTHER INFORMATION: Sushi 1 Delta Peptide

<400> SEQUENCE: 4

Gly Phe Lys Leu Lys Gly Lys Ala Lys Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser

<210> SEQ ID NO 5
<211> LENGTH: 34
<212> TYPE: PRT
<213> ORGANISM: Artificial Sequence
<220> FEATURE:
<223> OTHER INFORMATION: Sushi 3 Delta Peptide

<400> SEQUENCE: 5

His Ala Glu His Lys Val Lys Ile Lys Val Lys Gln Lys Tyr Gly Gln
1               5                   10                  15

Phe Pro Gln Gly Thr Glu Val Thr Tyr Thr Cys Ser Gly Asn Tyr Phe
            20                  25                  30

Leu Met
```

-continued

```
<210> SEQ ID NO 6
<211> LENGTH: 34
<212> TYPE: PRT
<213> ORGANISM: Artificial Sequence
<220> FEATURE:
<223> OTHER INFORMATION: Sushi 4 Peptide

<400> SEQUENCE: 6

Arg Ala Glu His Lys Val Lys Lys Ile Val Lys Gln Leu Tyr Gly Gln
1               5                   10                  15

Phe Arg Gln Leu Thr Arg Val Thr Arg Thr Cys Ser Arg Phe Leu Arg
                20                  25                  30

Arg Met

<210> SEQ ID NO 7
<211> LENGTH: 24
<212> TYPE: PRT
<213> ORGANISM: Artificial Sequence
<220> FEATURE:
<223> OTHER INFORMATION: Sushi 5 Peptide

<400> SEQUENCE: 7

His Lys Val Lys Lys Ile Val Lys Gln Leu Tyr Arg Ala Glu His Lys
1               5                   10                  15

Val Lys Lys Ile Val Lys Gln Leu
                20

<210> SEQ ID NO 8
<211> LENGTH: 1019
<212> TYPE: PRT
<213> ORGANISM: Carcinoscorpius rotundicauda

<400> SEQUENCE: 8

Met Val Leu Ala Ser Phe Leu Val Ser Gly Leu Val Leu Gly Leu Leu
1               5                   10                  15

Ala Gln Lys Met Arg Pro Val Gln Ser Lys Gly Val Asp Leu Gly Leu
                20                  25                  30

Cys Asp Glu Thr Arg Phe Glu Cys Lys Cys Gly Asp Pro Gly Tyr Val
            35                  40                  45

Phe Asp Ile Pro Val Lys Gln Cys Thr Tyr Phe Tyr Arg Trp Arg Pro
        50                  55                  60

Tyr Cys Lys Pro Cys Asp Asp Leu Glu Ala Lys Asp Ile Cys Pro Lys
65                  70                  75                  80

Tyr Lys Arg Cys Gln Glu Cys Lys Ala Gly Leu Asp Ser Cys Val Thr
                85                  90                  95

Cys Pro Pro Asn Lys Tyr Gly Thr Trp Cys Ser Gly Glu Cys Gln Cys
            100                 105                 110

Lys Asn Gly Gly Ile Cys Asp Gln Arg Thr Gly Ala Cys Ala Cys Ala
        115                 120                 125

Asp Arg Tyr Glu Gly Val His Cys Glu Ile Leu Lys Gly Cys Pro Leu
    130                 135                 140

Leu Pro Ser Asp Ser Gln Val Gln Glu Val Arg Asn Pro Pro Asp Asn
145                 150                 155                 160

Pro Gln Thr Ile Asp Tyr Ser Cys Ser Pro Gly Phe Lys Leu Lys Gly
                165                 170                 175

Met Ala Arg Ile Ser Cys Leu Pro Asn Gly Gln Trp Ser Asn Phe Pro
            180                 185                 190

Pro Lys Cys Ile Arg Glu Cys Ala Met Val Ser Ser Pro Glu His Gly
        195                 200                 205
```

```
Lys Val Asn Ala Leu Ser Gly Asp Met Ile Glu Gly Ala Thr Leu Arg
    210                 215                 220

Phe Ser Cys Asp Ser Pro Tyr Tyr Leu Ile Gly Gln Glu Thr Leu Thr
225                 230                 235                 240

Cys Gln Gly Asn Gly Gln Trp Asn Gly Gln Ile Pro Gln Cys Lys Asn
                245                 250                 255

Leu Val Phe Cys Pro Asp Leu Asp Pro Val Asn His Ala Glu His Lys
            260                 265                 270

Val Lys Ile Gly Val Glu Gln Lys Tyr Gly Gln Phe Pro Gln Gly Thr
        275                 280                 285

Glu Val Thr Tyr Thr Cys Ser Gly Asn Tyr Phe Leu Met Gly Phe Asp
    290                 295                 300

Thr Leu Lys Cys Asn Pro Asp Gly Ser Trp Ser Gly Ser Gln Pro Ser
305                 310                 315                 320

Cys Val Lys Val Ala Asp Arg Glu Val Asp Cys Asp Ser Lys Ala Val
                325                 330                 335

Asp Phe Leu Asp Asp Val Gly Glu Pro Val Arg Ile His Cys Pro Ala
            340                 345                 350

Gly Cys Ser Leu Thr Ala Gly Thr Val Trp Gly Thr Ala Ile Tyr His
        355                 360                 365

Glu Leu Ser Ser Val Cys Arg Ala Ala Ile His Ala Gly Lys Leu Pro
    370                 375                 380

Asn Ser Gly Gly Ala Val His Val Val Asn Asn Gly Pro Tyr Ser Asp
385                 390                 395                 400

Phe Leu Gly Ser Asp Leu Asn Gly Ile Lys Ser Glu Leu Lys Ser
                405                 410                 415

Leu Ala Arg Ser Phe Arg Phe Asp Tyr Val Arg Ser Ser Thr Ala Gly
            420                 425                 430

Lys Ser Gly Cys Pro Asp Gly Trp Phe Glu Val Asp Glu Asn Cys Val
        435                 440                 445

Tyr Val Thr Ser Lys Gln Arg Ala Trp Glu Arg Ala Gln Gly Val Cys
    450                 455                 460

Thr Asn Met Ala Ala Arg Leu Ala Val Leu Asp Lys Asp Val Ile Pro
465                 470                 475                 480

Asn Ser Leu Thr Glu Thr Leu Arg Gly Lys Gly Leu Thr Thr Thr Trp
                485                 490                 495

Ile Gly Leu His Arg Leu Asp Ala Glu Lys Pro Phe Ile Trp Glu Leu
            500                 505                 510

Met Asp Arg Ser Asn Val Val Leu Asn Asp Asn Leu Thr Phe Trp Ala
        515                 520                 525

Ser Gly Glu Pro Gly Asn Glu Thr Asn Cys Val Tyr Met Asp Ile Gln
    530                 535                 540

Asp Gln Leu Gln Ser Val Trp Lys Thr Lys Ser Cys Phe Gln Pro Ser
545                 550                 555                 560

Ser Phe Ala Cys Met Met Asp Leu Ser Asp Arg Asn Lys Ala Lys Cys
                565                 570                 575

Asp Asp Pro Gly Ser Leu Glu Asn Gly His Ala Thr Leu His Gly Gln
            580                 585                 590

Ser Ile Asp Gly Phe Tyr Ala Gly Ser Ser Ile Arg Tyr Ser Cys Glu
        595                 600                 605

Val Leu His Tyr Leu Ser Gly Thr Glu Thr Val Thr Cys Thr Thr Asn
    610                 615                 620

Gly Thr Trp Ser Ala Pro Lys Pro Arg Cys Ile Lys Val Ile Thr Cys
```

```
            625                 630                 635                 640
        Gln Asn Pro Pro Val Pro Ser Tyr Gly Ser Val Glu Ile Lys Pro Pro
                        645                 650                 655

Ser Arg Thr Asn Ser Ile Ser Arg Val Gly Ser Pro Phe Leu Arg Leu
                        660                 665                 670

Pro Arg Leu Pro Leu Pro Leu Ala Arg Ala Ala Lys Pro Pro Pro Lys
                        675                 680                 685

Pro Arg Ser Ser Gln Pro Ser Thr Val Asp Leu Ala Ser Lys Val Lys
                        690                 695                 700

Leu Pro Glu Gly His Tyr Arg Val Gly Ser Arg Ala Ile Tyr Thr Cys
        705                 710                 715                 720

Glu Ser Arg Tyr Tyr Glu Leu Leu Gly Ser Gln Gly Arg Arg Cys Asp
                        725                 730                 735

Ser Asn Gly Asn Trp Ser Gly Arg Pro Ala Ser Cys Ile Pro Val Cys
                        740                 745                 750

Gly Arg Ser Asp Ser Pro Arg Ser Pro Phe Ile Trp Asn Gly Asn Ser
                        755                 760                 765

Thr Glu Ile Gly Gln Trp Pro Trp Gln Ala Gly Ile Ser Arg Trp Leu
                        770                 775                 780

Ala Asp His Asn Met Trp Phe Leu Gln Cys Gly Gly Ser Leu Leu Asn
        785                 790                 795                 800

Glu Lys Trp Ile Val Thr Ala Ala His Cys Val Thr Tyr Ser Ala Thr
                        805                 810                 815

Ala Glu Ile Ile Asp Pro Asn Gln Phe Lys Met Tyr Leu Gly Lys Tyr
                        820                 825                 830

Tyr Arg Asp Asp Ser Arg Asp Asp Tyr Val Gln Val Arg Glu Ala
                        835                 840                 845

Leu Glu Ile His Val Asn Pro Asn Tyr Asp Pro Gly Asn Leu Asn Phe
                        850                 855                 860

Asp Ile Ala Leu Ile Gln Leu Lys Thr Pro Val Thr Leu Thr Thr Arg
        865                 870                 875                 880

Val Gln Pro Ile Cys Leu Pro Thr Asp Ile Thr Thr Arg Glu His Leu
                        885                 890                 895

Lys Glu Gly Thr Leu Ala Val Val Thr Gly Trp Gly Leu Asn Glu Asn
                        900                 905                 910

Asn Thr Tyr Ser Glu Thr Ile Gln Gln Ala Val Leu Pro Val Val Ala
                        915                 920                 925

Ala Ser Thr Cys Glu Glu Gly Tyr Lys Glu Ala Asp Leu Pro Leu Thr
                        930                 935                 940

Val Thr Glu Asn Met Phe Cys Ala Gly Tyr Lys Lys Gly Arg Tyr Asp
        945                 950                 955                 960

Ala Cys Ser Gly Asp Ser Gly Gly Pro Leu Val Phe Ala Asp Asp Ser
                        965                 970                 975

Arg Thr Glu Arg Arg Trp Val Leu Glu Gly Ile Val Ser Trp Gly Ser
                        980                 985                 990

Pro Ser Gly Cys Gly Lys Ala Asn Gln Tyr Gly Gly Phe Thr Lys Val
                        995                 1000                1005

Asn Val Phe Leu Ser Trp Ile Arg Gln Phe Ile
                        1010                1015
```

ENHANCING ENDOTOXIN DETECTION

CROSS REFERENCE TO RELATED APPLICATIONS

This application is a divisional of U.S. application Ser. No. 12/193,169, filed Aug. 18, 2008, currently pending, which is herein incorporated by reference in its entirety.

BACKGROUND

Endotoxin, also known as lipopolysaccharide (LPS), is an integral component of the gram-negative bacterial cell membrane and is responsible for many, if not all, of the toxic effects that occur during gram-negative bacterial sepsis. LPS is a mixture of glycolipids consisting of a variable polysaccharide domain covalently bound to a conserved glucosamine-based phospholipid known as lipid A. LPS directly stimulates host monocytes and macrophages to secrete a wide array of inflammatory cytokines that include tumor necrosis factor-α (TNF-α), interleukins-1 (IL-1), and interleukin-8 (IL-8). Excessive release of these cytokines by host macrophages contributes to organ failure and death that occur after episodes of gram-negative bacterial sepsis. The pro-inflammatory bioactivities exhibited by LPS typically reside in the lipid A moiety.

SUMMARY

Provided herein are methods for detecting gram negative bacteria or lipopolysaccharide in a sample. For example, provide is a method for detecting gram negative bacteria or lipopolysaccharide in a sample comprising contacting the sample with one or more lipopolysaccharide binding polypeptides in the presence of an inactive acidic protease, and determining whether the one or more lipopolysaccharide binding polypeptides bind to the sample. Binding indicates the sample contains gram negative bacteria or lipopolysaccharide. Also provided herein are methods for detecting gram negative bacteria or lipopolysaccharide in a sample comprising contacting the sample with an active acidic protease under conditions that result in degradation of the proteins in the sample, contacting the sample with one or more lipopolysaccharide binding polypeptides in the presence of an inactive acidic protease, and determining whether the one or more lipopolysaccharide binding polypeptides bind to the sample.

Provided is a method for detecting gram negative bacteria or lipopolysaccharide in a sample comprising contacting the sample with an active acidic protease under conditions that result in degradation of the proteins in the sample, further contacting the sample with an amebocyte lysate, and determining whether a gelation reaction occurs in the amebocyte lysate.

Kits for detecting gram negative bacteria or lipopolysaccharide in a sample are provided. The kits comprise an acidic protease. The kits also comprise one or more amebocyte lysates and/or one or more lipopolysaccharide binding polypeptides.

The details of one or more aspects are set forth in the accompanying drawings and description below. Other features, objects, and advantages will be apparent from the description and drawings, and from the claims.

DESCRIPTION OF DRAWINGS

FIG. 1A is a graph representing the ability to recover 1 Endotoxin Unit (EU)/ml PPC spike before and after Pepsin digestion. Without Pepsin there is a 0% recovery indicating complete assay inhibition with intact Peptide X. Upon addition of Pepsin, Peptide X is degraded and PPC recovery increases to as much as 75%. Industry standards dictate that a PPC recovery in the 50-200% range is acceptable. FIG. 1B is a graph representing the ability to recover the 250 EU/ml (calculated) added to the Peptide X sample prior to incubation. As with the PPC recovery in FIG. 1A, samples with intact Peptide X result in 100% assay inhibition. Addition of Pepsin is accompanied by an increase in LPS recovery to 154 EU/ml.

DETAILED DESCRIPTION

Figure 1A:
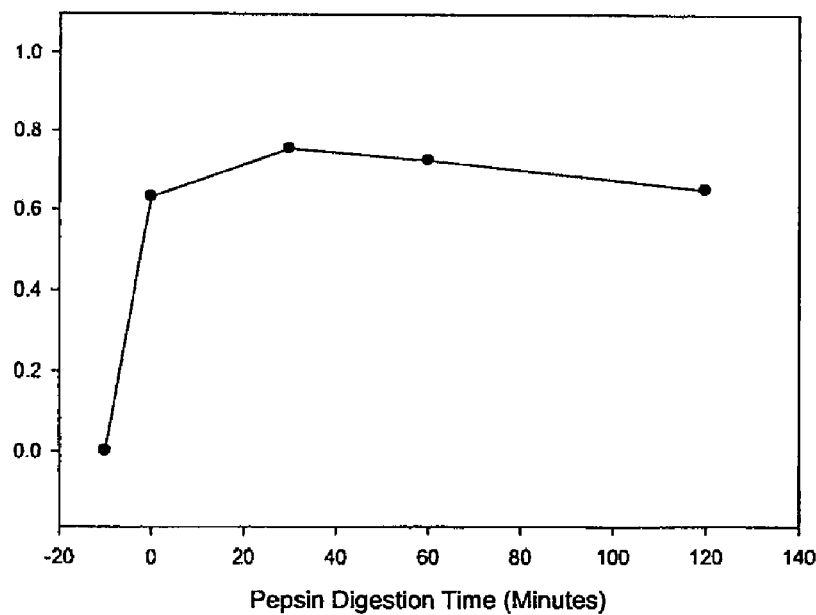
FIGS. 1A-1B show positive product control (PPC) recovery and lipopolysaccharide (LPS) recovery in peptide x sample. Data shown is from 60 minute PyroGene® (Lonza; Basel, Switzerland) incubation.

Since endotoxin contains a negative charge, a lipid and a carbohydrate, many proteins are known to bind endotoxin and affect the ability of assays to properly measure it. Specifical Factor C is a serine protease zymogen. It is the key enzyme in the *C. rotundicauda* amebocyte lysate (CAL) that is activated by LPS to initiate the coagulation cascade. Factor C activity is the basis of a sensitive assay for femtogram levels of endotoxin used in the quality control of pharmaceutical products. The importance of Factor C in the detection of endotoxin has led to the expression of recombinant Factor C, rFC, as an alternative source to alleviate the batch-to-batch and seasonal variation in the sensitivity of detection of endotoxin.

Inactive acidic proteases, such as inactive pepsin and inactive HIV protease, enhance the activity of Factor C by acting as a chaperone and maintaining Factor C in proper conformation. The ability of inactive pepsin and inactive HIV protease to act as chaperones has been described (Hulko et al., *Protein Science* 16:644-53 (2007)).

Provided herein are improved methods and kits for detecting gram negative bacteria or lipopolysaccharide in a sample. For example, provided herein are methods for detecting gram negative bacteria or lipopolysaccharide in a sample comprising contacting the sample with one or more lipopolysaccharide binding polypeptides in the presence of an inactive acidic protease, and determining whether the one or more lipopolysaccharide binding polypeptides bind to the sample. Binding indicates the sample contains gram negative bacteria or lipopolysaccharide. Optionally, the method further comprises inactivating the acidic protease prior to contacting the sample with the one or more lipopolysaccharide binding polypeptides. Optionally, the method further comprising contacting the sample with an active acidic protease under conditions that result in degradation of the proteins in the sample prior to contacting the sample with the one or more lipopolysaccharide binding polypeptides. Provided herein are methods for detecting gram negative bacteria or lipopolysaccharide in a sample comprising contacting the sample with an active acidic protease under conditions that result in degradation of the proteins in the sample, contacting the sample with one or more lipopolysaccharide binding polypeptides in the presence of an inactive acidic protease, and determining whether the one or more lipopolysaccharide binding polypeptides bind to the sample. Binding indicates the sample contains gram negative bacteria or lipopolysaccharide. Optionally, the method further comprises inactivating the acidic protease after contacting the sample with the active acidic protease. Optionally, a digestion buffer comprises the active acidic protease. Optionally, the acidic protease is inactivated by a pH of about 7.0.

Also provided is a method for detecting gram negative bacteria or lipopolysaccharide in a sample comprising contacting the sample with an active acidic protease under conditions that result in degradation of the proteins in the sample, further contacting the sample with an amebocyte lysate, and determining whether a gelation reaction occurs in the amebocyte lysate. A gelation reaction indicates the sample contains gram negative bacteria or lipopolysaccharide. Optionally, the amebocyte lysate is selected from the group consisting of lysates of *Limulus polyphemus, Tachypleus tridentatus, Carcinoscorpius rotundicauda* and *Tachypleus gigas.*

Lipopolysaccharide binding polypeptides suitable for use in the provided methods and kits include lipopolysaccharide binding polypeptides of an amebocyte lysate. The amebocyte lysate is, optionally, selected from the group consisting of lysates of *Limulus polyphemus, Tachypleus tridentatus, Carcinoscorpius rotundicauda* and *Tachypleus gigas.* Optionally, the one or more lipopolysaccharide binding polypeptides are polypeptides comprising a lipopolysaccharide binding domain of a Factor C protein. The endotoxin/lipid A-binding domain of Factor C lies within the amino terminal portion of the protein encompassed by rFCES; that is, the first 350 amino acids, numbered as in SEQ ID NO:8. The Factor C protein and its domains, including sushi domains, are described in U.S. Pat. No. 6,719,973, which is incorporated by reference herein in its entirety. U.S. Pat. No. 6,719,973 also discloses sushi peptides of the Factor C protein and methods for making and using the sushi peptides. Thus, the lipopolysaccharide binding domain of a Factor C protein is optionally a sushi domain or peptide. The lipopolysaccharide binding domain of a Factor C protein is, for example, amino acids 1-333 of a Factor C protein (e.g., amino acids 1-333 of SEQ ID NO:8), amino acids 29-330 of SEQ ID NO:8, a sushi 1 domain of a Factor C protein (e.g., amino acids 29-201 of SEQ ID NO:8), a sushi 2 domain of a Factor C protein (e.g., amino acids 195-260 of SEQ ID NO:8), a sushi 3 domain of a Factor C protein (e.g., amino acids 264-330 of SEQ ID NO:8), a sushi 1 peptide (SEQ ID NO:1), a sushi 2 peptide (SEQ ID NO:2), a sushi 3 peptide (SEQ ID NO:3), a sushi 1Δ peptide (SEQ ID NO:4), a sushi 3Δ peptide (SEQ ID NO:5), a sushi 4 peptide (SEQ ID NO:6) or a sushi 5 peptide (SEQ ID NO:7).

Optionally, the step of contacting the sample with the one or more lipopolysaccharide binding polypeptides comprises contacting the sample with a dimer or a tetramer comprising a lipopolysaccharide binding domain of a Factor C protein. As used herein, the phrase Factor C dimer refers to two molecules of a Factor C protein or portion thereof linked together. The provided Factor C dimers comprise a first and a second polypeptide, wherein the first and second polypeptides each comprise a lipopolysaccharide binding domain of a Factor C protein. Optionally, the first and second polypeptide are the same or different polypeptides. Optionally, the lipopolysaccharide binding domain of a Factor C protein is a sushi peptide. The sushi peptide can be a sushi 1 peptide (SEQ ID NO:1), a sushi 2 peptide (SEQ ID NO:2), a sushi 3 peptide (SEQ ID NO:3), a sushi 1Δ peptide (SEQ ID NO:4), a sushi 3Δ peptide (SEQ ID NO:5), a sushi 4 peptide (SEQ ID NO:6) or a sushi 5 peptide (SEQ ID NO:7). Optionally, the sushi peptide is a sushi 3 peptide or a sushi 3Δ peptide. Optionally, the polypeptides of the Factor C dimer are linked by disulfide bonds. A disulfide bond is a bond between cysteine residues. Optionally, each of the first and second polypeptides that comprise the Factor C dimer consists of SEQ ID NOs:1, 2, 3, 4, 5, 6 or 7.

The term protein, peptide, polypeptide, or peptide portion is used broadly herein to mean two or more amino acids linked by a peptide bond. It should be recognized that the terms peptide and polypeptide are not used herein to suggest a particular size or number of amino acids comprising the molecule and that a peptide can contain up to several amino acid residues or more. The provided peptides are produced by a proteolytic reaction on a polypeptide, i.e., a peptide produced upon cleavage of a peptide bond in the polypeptide. The provided peptides are optionally produced using methods of chemical synthesis or methods of recombinant DNA technology, to produce a synthetic polypeptide. For example, the provided peptides are synthesized using stepwise solid phase peptide synthesis on 2-chlorotrityl resin using standard Fmoc protecting groups and pseudo-prolines. Alternatively, the peptides are synthesized by combining two or more smaller peptides that have been chemically synthesized.

Nucleic acids that encode the aforementioned peptide sequences, variants and fragments thereof are also disclosed. These sequences include all degenerate sequences related to a specific polypeptide sequence, i.e., all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every sequence is in fact disclosed and described herein through the disclosed protein sequence. A wide variety of expression systems are used to produce Factor C peptides as well as fragments, isoforms, and variants.

The nucleic acid sequences provided herein are examples of the genus of nucleic acids and are not intended to be limiting. Also provided are expression vectors comprising nucleic acids that encode the peptide sequences, variants or fragments thereof, wherein the nucleic acids are operably linked to an expression control sequence. Further provided are cultured cells comprising the expression vectors. Such expression vectors and cultured cells can be used to make the provided peptides.

By isolated or purified is meant a composition (e.g., a polypeptide or nucleic acid) that is substantially free from other materials, including materials with which the composition is normally associated in nature. The polypeptides of the invention, or fragments thereof, are obtained, for example, by extraction from a natural source, by expression of a recombinant nucleic acid encoding the polypeptide (e.g., in a cell or in a cell-free translation system), or by chemically synthesizing the polypeptide.

In the provided methods and kits, the lipopolysaccharide binding polypeptides are optionally labeled with a detectable moiety or further comprise a reporter protein or affinity tag. The lipopolysaccharide binding polypeptides are directly labeled or to indirectly labeled (e.g., by a secondary or tertiary antibody that is labeled with a detectable moiety). Numerous labels are available including, but not limited to radioisotopes, fluorescent labels, and enzyme-substrate labels. Radioisotopes include, for example, $^{35}S$, $^{14}C$, $^{125}I$, $^{3}H$, and $^{131}I$. Fluorescent labels include, for example, rare earth chelates (europium chelates), fluorescein and its derivatives, rhodamine and its derivatives, dansyl, Lissamine, phycoerythrin and Texas Red. The labels are optionally conjugated to the antigen binding partner using the techniques disclosed in Current Protocols in Immunology, Volumes 1 and 2, Coligen et al., Ed., Wiley-Interscience, New York, N.Y., Pubs., (1991), for example.

When using enzyme-substrate labels, the enzyme preferably catalyses a chemical alteration of the chromogenic substrate, which can be measured using various techniques. For example, the enzyme catalyzes a color change in a substrate, which can be measured spectrophotometrically. Alternatively, the enzyme alters the fluorescence or chemiluminescence of the substrate. The chemiluminescent substrate becomes electronically excited by a chemical reaction and then emits light which can be measured (using a chemiluminometer, for example), or donates energy to a fluorescent acceptor. Examples of enzymatic labels include luciferases (e.g., firefly luciferase and bacterial luciferase), luciferin, 2,3-dihydrophthalazinediones, malate dehydrogenase, urease, peroxidase such as horseradish peroxidase (HRP), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as unease and xanthine oxidase), lactoperoxidase, microperoxidase, and the like. Techniques for conjugating enzymes are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73: 147-166 (1981). Examples of enzyme-substrate combinations include, for example, horseradish peroxidase (HRP) with hydrogen peroxidase as a substrate, alkaline phosphatase (AP) with para-Nitrophenyl phosphate as chromogenic substrate, and β-D-galactosidase (β-D-Gal) with a chromogenic substrate (e.g. p-nitrophenyl-β-D-galactosidase) or fluorogenic substrate 4-methylumbelliferyl-β-D-galactosidase.

An assay is optionally employed wherein the lipopolysaccharide binding polypeptides are attached to a solid support, such as, for example, a column, chip, or plate. The solid support is optionally a mobile solid support (e.g., a bead). A sample derived from the subject or control is passed over (i.e., contacted with) the solid support. Labeled lipopolysaccharide binding polypeptides are then added to the solid support. The amount of label detected that is attached to the target is correlated to a quantity of target in the sample. For example, a lipopolysaccharide binding polypeptide is immobilized on the bottom of a microtiter plate. A sample to be tested is then added to the microtiter plate under conditions that allow binding of the lipopolysaccharide binding polypeptide to gram negative bacteria, endotoxin or lipopolysaccharide if present in the sample. A second lipopolysaccharide binding polypeptide that is labeled with, for example, biotin, is added to the microtiter plate. The labeled polypeptide is detected with avidin coupled to alkaline phosphatase. The avidin coupled to alkaline phosphatase detects bound and labeled polypeptide by liberating p-nitrophenol from a p-nitrophenylphosphate (pNA) substrate producing a yellow color that can be measured at 405 nm.

FACS sorting is used to detect and quantitate, for example, fluorescently labeled beads. For example, the lipopolysaccharide binding polypeptide is linked to a bead. The beads are then contacted with a sample to be tested. A second lipopolysaccharide binding polypeptide that is labeled with, for example, a fluorescent label is added to the beads that have been contacted with the test sample. The bound, labeled beads are then detected and quantitated using a FACS sorter on the basis of one or more fluorescent labels. Optionally, the beads are magnetic beads or fluorescent beads. For example, the lipopolysaccharide binding polypeptide is linked to a mobile solid support such as a bead, which can be added to a biological sample, such as whole blood or blood products like serum, and removed by centrifugation. Optionally, the lipopolysaccharide binding polypeptide is linked to a magnetic bead, such as an iron bead, and removed by a magnetic field.

By way of another example, the lipopolysaccharide binding polypeptide is immobilized on an immobile solid support, such as, for example, a column, filter or membrane. Thus, the lipopolysaccharide binding polypeptide is immobilized, for example, on a hemodialysis membrane or filtration system to remove bacteria and/or endotoxin from whole blood or blood products. Thus, support as used herein refers to any support matrix, such as those solid supports known in the art, which serve to immobilize the lipopolysaccharide binding polypeptide. Suitable supports include, but are not limited to, glass, agarose, plastic, silica, polyacrylamide, hydrogels, gels, membranes, filters, meshes, beads or particles comprised of or coated with cellulose, acrylates, polyacrylates, polyhydroxymethacrylates, polystyrene, dextran, agarose, polysaccharides, hydrophilic vinyl polymers, polymerized derivatives, as well as any porous or non-porous matrices.

Optionally, the lipopolysaccharide binding polypeptides further comprise a reported protein or affinity tag. Suitable reporter proteins include, for example, green fluorescent protein (GFP), alkaline phosphatase, peroxidase and luciferase. Affinity tags include, but are not limited to, polyhistidine, avidin, streptavidin and biotin.

The sample is optionally a biological sample. As used herein, a biological sample subjected to testing is a sample derived from a subject such as a mammal or human and includes, but is not limited to, any biological fluid, including a bodily fluid. Examples of bodily fluids include, but are not limited to, whole blood, serum, urine, saliva, tissue infiltrate, pleural effusions, lung lavage fluid, and the like. The biological fluid includes a cell culture medium or supernatant of cultured cells. For example, the sample can be a blood sample or a serum sample. Optionally, the sample is a liquid sample, such as water or other agents used, for example, in research or clinical laboratories or hospitals. Optionally, the sample is an environmental sample including, but not limited to, fluid, waste, water and rain samples. Optionally, the environmental sample is obtained from a surface, for example, in a hospital, for analysis in the provided methods. For example, a sample can be obtained from a device used in a hospital, clinical or laboratory setting and analyzed for the presence of gram negative bacteria. Optionally, the sample is diluted in solution prior to analysis. Optionally, the sample to be tested comprises a polypeptide in need of degradation. Thus, for example, the sample comprises a polypeptide that inhibits standard endotoxin assays, for example, a serine protease inhibitor.

As used herein, acid, acidic, aspartic or aspartic acid proteases refer to proteases active at low pH. For example, the protease is active at a pH from about 0.0 to about 6.0 or any pH between 0.0 and 6.0, inclusive. Such proteases are inactive at a pH of about 6.0 to about 14.0. As used herein, an inactive acidic protease refers to a protease without protealytic activity (i.e., a protease that is unable to cleave an amino acid sequence such as a polypeptide or protein). As used herein, an active acidic protease refers to a protease with proteolytic activity (i.e., a protease that is able to cleave an amino acid sequence). By way of example, an active acidic protease can be inactivated by a pH of 6.5 or higher (i.e., the protease is in a solution with a pH of 6.5 or higher). The pH of a solution can be altered by addition of chemicals to a solution. For example, hydrochloric acid can be used to reduce pH and sodium hydroxide can be used to raise pH. Phosphoric acid can be used to maintain a pH of about 6.5. Optionally, a pepsin inhibitor is used to inactivate pepsin. Pepsin inhibitors include, but are not limited to, acetamidine, N-acetyl-D-phenyalanyl-L-diiodotyrosine, N-acetyl-L-phenyalanyl-D-phenylalaine, p-aminobenzamidine, benzamidine, butyamine, diazoketones, ethylamine, pepstatin, and phenylactamidine.

Acid or acidic proteases, such as endopeptidases, are known and have been grouped into three families, namely, pepsin (A1), retropepsin (A2), and enzymes from pararetroviruses (A3). The members of families A1 and A2 are known to be related to each other, while those of family A3 show some relatedness to A1 and A2. Microbial acid proteases exhibit specificity against aromatic or bulky amino acid residues on both sides of the peptide bond, which is similar to pepsin, but their action is less stringent than that of pepsin. Acid proteases include microbial, fungal, viral, animal and plant acidic proteases. Microbial aspartic proteases can be broadly divided into two groups, (i) pepsin-like enzymes produced by *Aspergillus, Penicillium, Rhizopus*, and *Neurospora* and (ii) rennin-like enzymes produced by *Endothia* and *Mucor* spp (Rao et al., *Microbiology and Molecular Biology* 62(3):597-635 (1998); Richter et al., *Biochem. J.* 335:481-90 (1998)). Examples of acidic proteases include, but are not limited to, pepsins, including pepsins A, B and C; rennin; chymosin; plasmepsin; cathepsins, such as, for example, cathepsin D and cathepsin E; human urinary acid protease; and viral proteases like HIV protease. Fungal proteases include, but are not limited to, fungal proteases derived from *Neurospora oryzae, Mucor pusillus, Mucor miehei, Aspergillus niger, Rhizopus chinensis*, or *Endothia parasitica*. Microbial proteases include, but are not limited to, yeast proteinase A, aspergillopepsinogen, rhizopuspepsin, penicillopepsin, and endothiapepsin.

Kits for detecting gram negative bacteria or lipopolysaccharide are provided. The kits comprise an acidic protease. The kits also comprise one or more amebocyte lysates and/or one or more lipopolysaccharide binding polypeptides. Optionally, the lipopolysaccharide binding polypeptides are lipopolysaccharide binding polypeptides of an amebocyte lysate. Optionally, the amebocyte lysate is selected from the group consisting of lysates of *Limulus polyphemus, Tachypleus tridentatus, Carcinoscorpius rotundicauda* and *Tachypleus gigas*. As discussed above, the acidic protease can be any acidic protease. For example, the acidic protease is selected from the group consisting of pepsin, rennin, chymosin, plasmepsin, cathepsin D, cathepsin E, human urinary acid protease, HIV protease, *Neurospora oryzae* protease, *Mucor pusillus* protease, *Mucor miehei* protease, *Aspergillus niger* protease, *Rhizopus chinensis* protease, *Endothia parasitica* protease, yeast proteinase A, aspergillopepsinogen, rhizopuspepsin, penicillopepsin, and endothiapepsin. As also discussed above, the one or more lipopolysaccharide binding polypeptides are, for example, polypeptides comprising a lipopolysaccharide binding domain of a Factor C protein. The kits optionally comprise solid supports such as, for example, a column, plate, chip, or mobile solid support. The mobile solid support is, for example, a magnetic or fluorescent bead. Optionally, the kits further comprising one or more buffers, such as, for example, a digestion buffer. Optionally, the one or more amebocyte lysates and acidic protease are in the same or separate containers. Optionally, the one or more lipopolysaccharide binding polypeptides and the acidic protease are in the same or separate containers. Optionally, the acidic protease is inactive. Optionally, the kits comprise an active acidic protease and an inactive acidic protease, wherein the active acidic protease is the same as or different from the inactive acidic protease. Thus, for example, if the proteases are different, the active protease is pepsin and the inactive protease is chymosin.

Disclosed are materials, compositions, and components that can be used for, can be used in conjunction with, can be used in preparation of, or are products of the disclosed methods and compositions. These and other materials are disclosed herein, and it is understood that when combinations, subsets, interactions, groups, etc. of these materials are disclosed that, while specific reference to each various individual and collective combinations and permutation of these compounds may not be explicitly disclosed, each is specifically contemplated and described herein. For example, if a method is disclosed and discussed and a number of modifications can be made to materials used in the method or in the steps of the method, each and every combination and permutation of the method and the modifications that are possible are specifically contemplated unless specifically indicated to the contrary. Likewise, any subset or combination of these is also specifically contemplated and disclosed. Thus, if there is a variety of additional steps that can be performed in a method, it is understood that each of these additional steps can be performed with any specific method steps or combination of method steps of the disclosed methods, and that each such combination or subset of combinations is specifically contemplated and should be considered disclosed. Thus, a number of aspects have been described. Nevertheless, it will be understood that various modifications may be made. Furthermore, when one characteristic or step is described, it can be combined with any other characteristic or step herein even if the combination is not explicitly stated. Accordingly, all combination of disclosed agents, steps and characteristics are provided even in the absence of explicit disclosure herein.

Ranges may be expressed herein as from about one particular value, and/or to about another particular value. When such a range is expressed, this includes from the one particular value and/or to the other particular value. Similarly, when values are expressed as approximations, by use of the antecedent about, it will be understood that the particular value is disclosed.

Throughout this application, various publications are referenced. The disclosures of these publications in their entireties are hereby incorporated by reference into this application.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and materials provided herein.

EXAMPLES

Example 1

Use of Pepsin to Enhance Methods of Detecting Endotoxin in a Sample

The following experiments compared the recovery of native or endogenous lipopolysaccharide (LPS) in a protein sample before and after digestion with pepsin. Several proteins are known to bind LPS and affect their ability to be properly measured. Treatment of such samples with pepsin via the following protocol increases the accuracy of *Limulus Amebocyte* Lysate (LAL) and recombinant Factor C (rFC) assays as well as cytokine ELISA assays. The protocol outlines the procedure used to evaluate a peptide sample (Peptide X) and a protein sample (bovine serum albumin (BSA)). Both Peptide X and BSA contained negligible amounts of endogenous LPS, so a defined amount of *E. coli* O55:B5 LPS was added.

Pepsin Stock Preparation. To create a 5% pepsin stock solution, 250 mg of pepsin was added to 5 ml of digestion buffer (20 mM sodium acetate, pH 4.5). This mixture was vortexed for several minutes until all of the pepsin went into solution. The pepsin was then stored at 4° C.

LPS Stock Preparation. To create different concentrations of LPS stock solutions, 1 ml of endotoxin-free water was added to a 5 mg vial of *E. coli* O55:B5 LPS to create a 5 mg/ml (50,000,000 Endotoxin Units (EU)/ml) stock solution. This mixture was vortexed for several minutes until all of the LPS went into solution. To create a 500,000 EU/ml solution, 10 µl of the 5 mg/ml LPS solution was added to 990 µl of endotoxin-free water. To create a 50,000 EU/ml solution, 100 µl of the 5 mg/ml LPS solution was added to 900 µl of endotoxin-free water. To create a 10,000 EU/ml solution, 200 µl of the 5 mg/ml LPS solution was added to 800 µl of endotoxin-free water.

Peptide X and Lipopolysaccharide (LPS) Sample Preparation. Since Peptide X contained a negligible amount of endogenous LPS, a defined amount of *E. coli* O55:B5 LPS was added to carry out the experiment. Peptide X was obtained as a 20 mg/ml stock solution. A 0.1 mg/ml Peptide X, 250 EU/mL LPS solution was made by adding 10 µl of the 20 mg/ml Peptide X solution and 10 µl of the 50,000 EU/ml LPS stock solution to 1980 µl of digestion buffer (20 mM sodium acetate, pH 4.5).

Pepsin digestion, preparation for PyroGene® assay (Lonza; Basel, Switzerland) and PyroGene® assay (Lonza; Basel, Switzerland). Pepsin digestion occurs at 37° C. To perform these experiments, a water bath was set to 37° C. To assay different time points, 270 µl of the Peptide X and LPS solution was aliquoted into six endotoxin-free glass dilution tubes. 30 µl of 5% pepsin were added to each sample, and the sample was vortexed. The samples were incubated at 37° C. for 0, 15, 30, 60, and 120 minutes. A control sample was treated with 30 µl of digestion buffer instead of pepsin and was not incubated at 37° C. The 0 minute time point sample was mixed with pepsin but was not incubated at 37° C.

The samples were then diluted 100-fold in endotoxin-free water. Briefly, 50 µl of each sample was diluted in 450 µl of endotoxin-free water for a 1:10 dilution, and 50 µl of the 1:10 dilution was diluted in 450 µl of endotoxin-free water for a 1:100 dilution. Thus the final concentrations of the samples was 1:100.

Figure 1B:
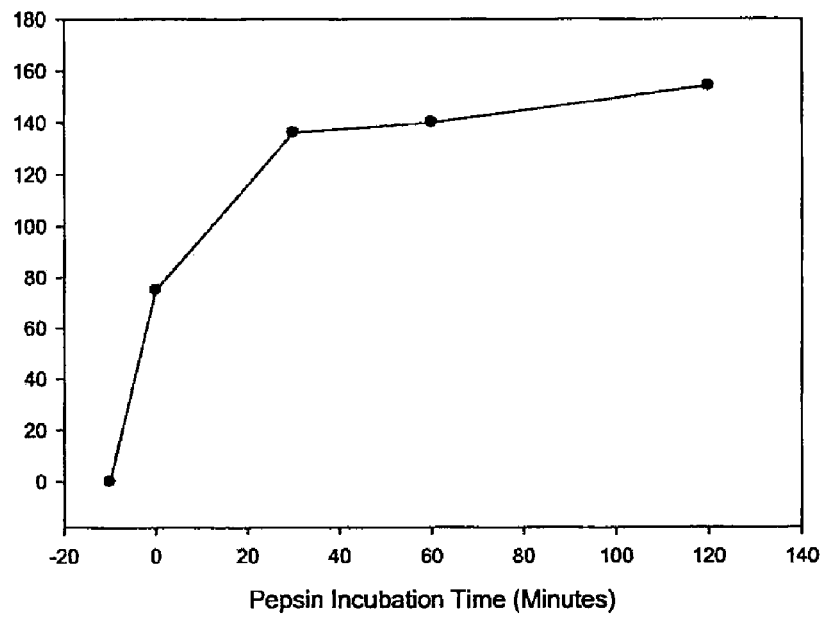

The PyroGene® assay (Lonza; Basel, Switzerland) was carried out according to manufacturer's protocols. LPS standards were created according to manufacturer's protocols. Each sample was tested both with and without a 1 EU/ml Positive Product Control (PPC) LPS spike. Samples with a 1 EU/ml PPC LPS spike were created by taking 45 µl of the sample and adding 5 µl of 10 EU/ml LPS. Each sample was added to 50 µl of PyroGene® working reagent (20 µl of recombinant Factor C (rFC) assay buffer, 5 µl rFC enzyme solution, and 25 µl fluorogenic substrate). The sample and working reagent were added to a single well of a Corning® (Corning Incorporated Life Sciences; Lowell, Mass.) 3604 Assay Plate and incubated in a BioTek Synergy 2 Plate Reader (BioTek; Winooski, Vt.) at 37° C. Fluorescence readings were made at 15, 30, 45, and 60 minute time points. Results are shown in Table 1 and FIG. 1.

TABLE 1

Fluorescence data at 60 minute PyroGene ® (Lonza; Basel, Switzerland) incubation.

| [Pepsin] | Digestion Time | Measured LPS Content | 1 EU/ml PPC Recovery |
| --- | --- | --- | --- |
| 0% | 0' | 0 EU/ml | 0 EU/ml |
| 0.5% | 0' | 75 EU/ml | 0.631 EU/ml |
| 0.5% | 30' | 136 EU/ml | 0.755 EU/ml |
| 0.5% | 60' | 140 EU/ml | 0.726 EU/ml |
| 0.5% | 120' | 154 EU/ml | 0.652 EU/ml |

Data were gathered for Peptide X and LPS samples tested with and without a 1 EU/ml PPC LPS spike. Without pepsin there is a 0% recovery indicating a complete assay inhibition with intact Peptide X. Upon addition of pepsin, Peptide X is degraded and PPC recovery increases to as much as 75%.

BSA and LPS Sample Preparation. Since BSA contains a negligible amount of endogenous LPS, a defined amount of *E. coli* O55:B5 LPS was added to carry out the experiment. A 1 mg/ml BSA, 100 EU/ml LPS solution was made by adding 20 µl of a 100 mg/ml BSA solution and 20 µl of a 10,000 EU/ml LPS stock solution to 1960 µl of digestion buffer (20 mM sodium acetate, pH 4.5).

Figure 2:
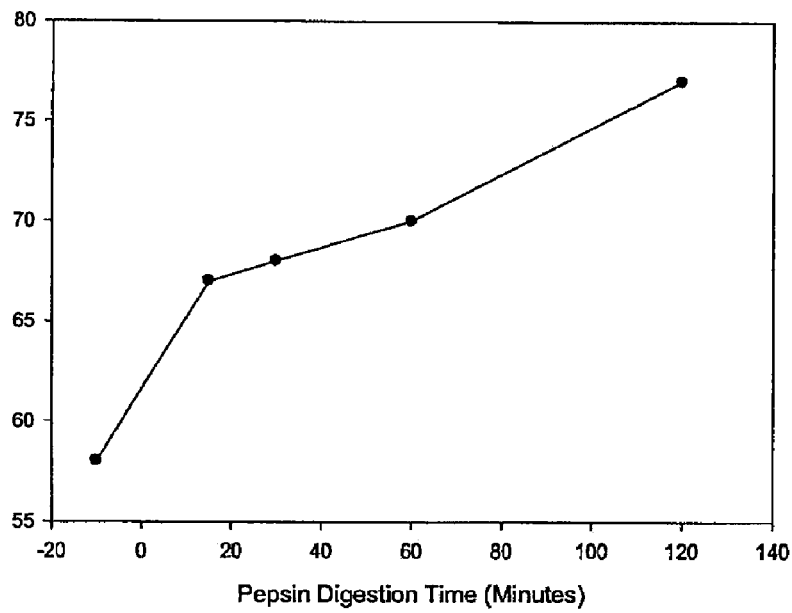
FIG. 2 is a graph showing LPS recovery in bovine serum albumin (BSA) sample. Data shown is from the 60 minute PyroGene® (Lonza; Basel, Switzerland) incubation. This graph represents the ability to recover the 100 EU/ml (calculated) LPS added to the BSA sample prior to incubation. With BSA, PPC recovery was sufficient in all samples, including non-digested BSA. The sample with intact BSA showed 58 EU/ml. Addition of Pepsin is accompanied by a steady increase in LPS recovery to 77 EU/ml, indicating a 33% increase in sensitivity in samples treated with Pepsin.

Pepsin digestion, preparation for PyroGene® assay (Lonza; Basel Switzerland), and PyroGene® assay (Lonza; Basel, Switzerland). The pepsin digestion, preparation for PyroGene® assay (Lonza; Basel, Switzerland), and the PyroGene® assay (Lonza; Basel, Switzerland) were carried out as described above for the Peptide X and LPS sample. Results are shown in Table 2 and FIG. 2.

TABLE 2

Fluorescence data at 60 minute PyroGene ® (Lonza; Basel, Switzerland) incubation.

| [Pepsin] | Digestion Time | Measured LPS Content |
|---|---|---|
| 0% | 0' | 58 EU/ml |
| 0.5% | 15' | 67 EU/ml |
| 0.5% | 30' | 68 EU/ml |
| 0.5% | 60' | 70 EU/ml |
| 0.5% | 120' | 77 EU/ml |

Data were gathered for BSA and LPS samples treated with pepsin. The sample with untreated BSA and LPS showed 58 EU/ml. Addition of pepsin increased LPS recovery to 77 EU/ml, indicating a 33% increase in sensitivity.

Example 2

Use of Pepsin to Increase Sensitivity of Methods of Detecting Endotoxin

The following experiments compare a series of LPS dilutions in water to a similar series containing a defined amount of pepsin. This data shows pepsin enhances the activity of the rFC Enzyme in the Lonza PyroGene® assay and results in an increase in sensitivity. This allows LPS detection below the current 0.01 EU/ml LPS concentration.

Pepsin Stock Preparation. To create a 5% stock solution of pepsin, 250 mg of pepsin was dissolved in 5 ml of digestion buffer (20 mM sodium acetate, pH 4.5). The mixture was vortexed until all the pepsin went into solution. The 5% pepsin solution was stored at 4° C.

LPS Sample Preparation. To create a series of LPS dilutions, a Lonza® (Lonza; Basel, Switzerland) LPS stock (20 EU/ml) was serially diluted. A 10 EU/ml LPS solution was created by diluting 200 µl of water with 200 µl of Lonza® stock (Lonza; Basel, Switzerland) for a final volume of 400 µl. A 1 EU/ml LPS solution was created by adding 50 µl of the 10 EU/ml LPS solution to 450 µl of water for a final volume of 500 µl. A 0.1 EU/ml LPS solution was created by adding 50 µl of the 1 EU/ml LPS solution to 450 µl of water for a final volume of 500 µl. A 0.01 EU/ml LPS solution was created by adding 50 µl of a 0.1 EU/ml LPS solution to 450 µl of water for a final volume of 500 µl.

LPS and Pepsin Sample Preparation. To create the same series of LPS dilutions that also contain 0.05% pepsin, two stock solutions of pepsin were made. A 0.1% stock solution of pepsin was made by adding 196 µl of water to 4 µl of 5% pepsin for a final volume of 200 µl. A 0.05% stock solution of pepsin was made by adding 1782 µl of water with 18 µl of 5% pepsin for a final volume of 1800 µl. 200 µl of the 0.1% pepsin solution was added to 200 µl of Lonza® (Lonza; Basel, Switzerland) LPS stock (20 EU/ml) to give 400 µl of a 10 EU/ml LPS, 0.05% pepsin solution. The 0.05% stock solution of pepsin was divided equally (450 µl) into 4 tubes. A 1 EU/ml LPS, 0.05% pepsin solution was created by adding 50 µl of the 10 EU/ml LPS, 0.05% pepsin solution to 450 µl of a 0.05% pepsin solution. A 0.1 EU/ml LPS, 0.05% pepsin solution was created by adding 50 µl of the 1 EU/ml LPS, 0.05% pepsin solution to 450 µl of a 0.05% pepsin solution. A 0.01 EU/ml LPS, 0.05% pepsin solution was created by adding 50 µl of the 0.1 EU/ml LPS, 0.05% pepsin solution to 450 µl of a 0.05% pepsin solution. A 0.001 EU/ml LPS, 0.05% pepsin solution was created by adding 50 µl of the 0.01 EU/ml LPS, 0.05% pepsin solution to 450 µl of a 0.05% pepsin solution.

Figure 3:
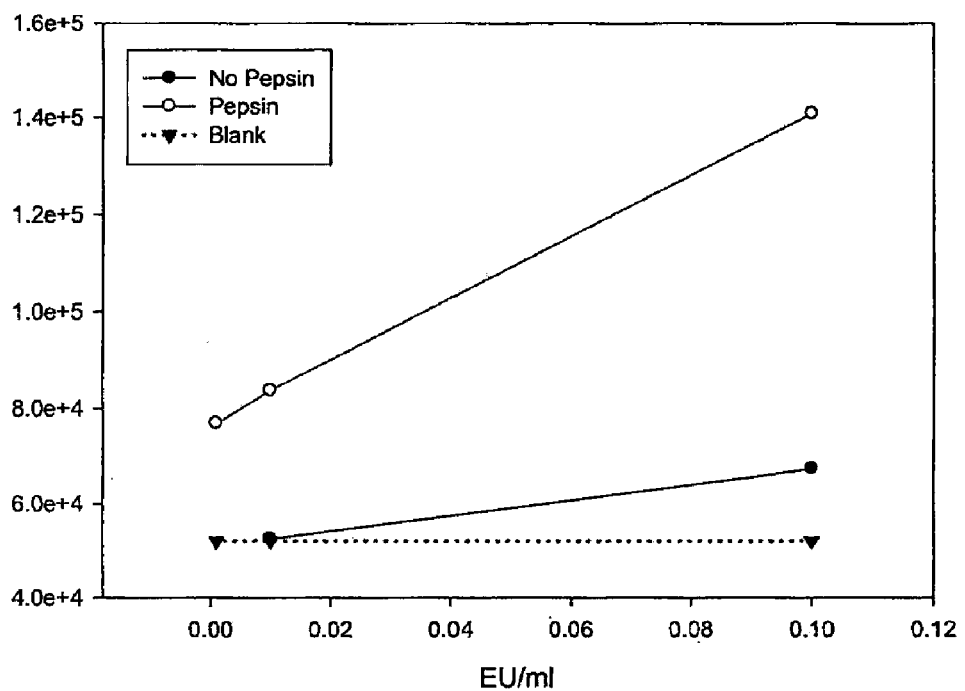
FIG. 3 is a graph showing the effect of pepsin on recombinant Factor C (rFC) activity. Data shown is from the 60 minute PyroGene® (Lonza; Basel, Switzerland) incubation. Solid black line with closed black circles for data points indicates results from LPS in water. Solid black line with open circles for data points indicates results from LPS in water containing 0.05% Pepsin. Dotted black line with triangles for data points indicates the value of water. Treatment with Pepsin enhances the activity of the rFC Enzyme as evidenced by the increase in fluorescene.

PyroGene® assay (Lonza; Basel, Switzerland). To test the endotoxin content of the samples prepared above, the PyroGene® assay (Lonza; Basel, Switzerland) was performed according to the manufacturer's specifications. Briefly, 50 µl of each sample was mixed with 50 µl of Pyrogene® (Lonza; Basel, Switzerland) working reagent (20 µl rFC assay buffer, 5 µl rFC enzyme solution, and 25 µl fluorogenic substrate) and was added to a single well of a Corning® (Corning Incorporated Life Sciences; Lowell, Mass.) 3604 Assay Plate. The plate was incubated in a BioTek Synergy 2 Plate Reader (BioTek; Winooski, Vt.) at 37° C. and fluorescence readings were taken at 15, 30, 45, and 60 minute time points. Results are shown in Table 3 and in FIG. 3.

TABLE 3

Fluorescence data at 60 minute PyroGene ® (Lonza; Basel, Switzerland) incubation.

| Sample | Fluorescence |
|---|---|
| 10 EU/ml in water | 1,012,941 |
| 1 EU/ml in water | 214,209 |
| 0.1 EU/ml in water | 67,374 |
| 0.01 EU/ml in water | 52,604 |
| 10 EU/ml in water with 0.05% Pepsin | 3,161,479 |
| 1 EU/ml in water with 0.05% Pepsin | 586,139 |
| 0.1 EU/ml in water with 0.05% Pepsin | 140,712 |
| 0.01 EU/ml in water with 0.05% Pepsin | 83,678 |
| 0.001 EU/ml in water with 0.05% Pepsin | 76,873 |
| Water | 52,096 |

Data were gathered for serial dilutions of untreated and treated LPS samples. Samples were treated with 0.05% pepsin. Treated samples were more sensitive to recombinant Factor C as evidenced by the increase in fluorescence.

What is claimed is:

1. A method for detecting gram negative bacteria or lipopolysaccharide in a sample consisting of the steps of:
   (a) contacting the sample with an active acidic protease under conditions that result in degradation of the proteins in the sample;
   (b) further contacting the sample with an amebocyte lysate after step (a), wherein the sample comprises the degraded proteins; and
   (c) determining whether a gelation reaction occurs in the amebocyte lysate, a gelation reaction indicating the sample of step (b) contains gram negative bacteria or lipopolysaccharide.

2. The method of claim 1, wherein the amebocyte lysate is selected from the group consisting of lysates of *Limulus polyphemus*, *Tachypleus tridentatus*, *Carcinoscorpius rotundicauda* and *Tachypleus gigas*.

3. A method for detecting gram negative bacteria or lipopolysaccharide in a sample consisting of the steps of:
   (a) contacting the sample with an active acidic protease under conditions that result in degradation of the proteins in the sample;
   (b) inactivating the acidic protease after step (a);
   (c) further contacting the sample with an amebocyte lysate after step (b), wherein the sample comprises the degraded proteins; and
   (d) determining whether a gelation reaction occurs in the amebocyte lysate, a gelation reaction indicating the sample of step (c) contains gram negative bacteria or lipopolysaccharide.

4. The method of claim 3, wherein the acidic protease is inactivated by increasing the pH of the sample to a pH of 6.5 or higher.

5. A method for detecting gram negative bacteria or lipopolysaccharide in a sample consisting of the steps of:
   (a) contacting the sample with an active acidic protease under conditions that result in degradation of the proteins in the sample;
   (b) diluting the sample;
   (c) inactivating the acidic protease after step (a);
   (d) further contacting the sample with an amebocyte lysate after step (c), wherein the sample comprises the degraded proteins; and
   (e) determining whether a gelation reaction occurs in the amebocyte lysate, a gelation reaction indicating the sample of step (d) contains gram negative bacteria or lipopolysaccharide.

6. The method of claim 5, wherein the acidic protease is inactivated by increasing the pH of the sample to a pH of 6.5 or higher.

* * * * *